(12) United States Patent
Kim et al.

(10) Patent No.: US 11,266,845 B2
(45) Date of Patent: Mar. 8, 2022

(54) DEVICES, SYSTEMS, AND METHODS FOR CARDIAC RESYNCHRONIZATION THERAPY

(71) Applicant: EBR Systems, Inc., Sunnyvale, CA (US)

(72) Inventors: Steven Kim, Sunnyvale, CA (US); Parker Willis, Sunnyvale, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 40 days.

(21) Appl. No.: 16/773,599

(22) Filed: Jan. 27, 2020

(65) Prior Publication Data

US 2020/0238093 A1 Jul. 30, 2020

Related U.S. Application Data

(60) Provisional application No. 62/797,800, filed on Jan. 28, 2019.

(51) Int. Cl.
| | |
|---|---|
| *A61N 1/37* | (2006.01) |
| *A61N 1/375* | (2006.01) |
| *A61N 1/372* | (2006.01) |
| *A61N 1/378* | (2006.01) |

(52) U.S. Cl.
CPC ....... *A61N 1/3756* (2013.01); *A61N 1/37217* (2013.01); *A61N 1/37512* (2017.08); *A61N 1/3787* (2013.01)

(58) Field of Classification Search
CPC .............. A61N 1/3756; A61N 1/37512; A61N 1/37217
See application file for complete search history.

(56) References Cited

U.S. PATENT DOCUMENTS

| 7,610,092 | B2 | 10/2009 | Cowan et al. | |
|---|---|---|---|---|
| 8,364,276 | B2 | 1/2013 | Willis | |
| 8,588,926 | B2 | 11/2013 | Moore et al. | |
| 9,180,285 | B2 | 11/2015 | Moore et al. | |
| 2004/0172083 | A1* | 9/2004 | Penner ................ | A61N 1/3718 607/35 |
| 2006/0136004 | A1* | 6/2006 | Cowan ................ | A61N 1/3621 607/33 |
| 2007/0244521 | A1* | 10/2007 | Bornzin ............... | A61N 1/3622 607/9 |
| 2007/0293895 | A1 | 12/2007 | Cowan et al. | |

(Continued)

OTHER PUBLICATIONS

International Search Report and Written Opinion dated Apr. 23, 2020 in International Patent Application No. PCT/US20/15247, 10 pages.

*Primary Examiner* — Eric D. Bertram
(74) *Attorney, Agent, or Firm* — Perkins Coie LLP (57) ABSTRACT

The present technology generally includes devices, systems, and methods for providing electrical stimulation to the left ventricle of a human heart in a patient suffering from Left Bundle Branch Block (LBBB). In particular, the present technology includes an implantable receiver-stimulator and an implantable controller-transmitter for leadless electrical stimulation of the heart. The receiver-stimulator can include one or more sensors capable of detecting the electrical conduction of the heart and the receiver-stimulator can be configured to pace the stimulation of the left ventricle based off the sensed electrical conduction to achieve synchronization of the left and right ventricles.

11 Claims, 4 Drawing Sheets

(56) References Cited

U.S. PATENT DOCUMENTS

| | | |
|---|---|---|
| 2009/0264965 A1 | 10/2009 | Fowler et al. |
| 2011/0319956 A1 | 12/2011 | Zhu et al. |
| 2012/0150251 A1 | 6/2012 | Giftakis et al. |
| 2012/0290027 A1 | 11/2012 | Lian et al. |
| 2013/0123653 A1 | 5/2013 | Maskara et al. |
| 2013/0282073 A1 | 10/2013 | Cowan et al. |
| 2014/0018874 A1 | 1/2014 | Zhu et al. |

* cited by examiner

DEVICES, SYSTEMS, AND METHODS FOR CARDIAC RESYNCHRONIZATION THERAPY

CROSS-REFERENCE TO RELATED APPLICATION(S)

The present application claims priority to U.S. Provisional Patent Application No. 62/797,800, titled "DEVICES, SYSTEMS, AND METHODS FOR CARDIAC RESYNCHRONIZATION THERAPY," filed Jan. 28, 2019, which is incorporated herein by reference in its entirety.

TECHNICAL FIELD

The present technology relates generally to wireless acoustic stimulation systems, devices, and methods for stimulating biological tissues, and in particular to a system including a controller-transmitter that emits acoustic energy and a receiver-stimulator that converts acoustic energy received from the controller-transmitter into electrical energy. The receiver-stimulator and controller-transmitter can be implanted into the body of a patient and operate without a co-implant, such as a pacemaker.

BACKGROUND

Patients suffering from heart failure or other cardiovascular related diseases can benefit from cardiac resynchronization therapy. In cardiac resynchronization therapy, electrodes are inserted into the left and right ventricles of the heart and provide stimulation to coordinate the function of the left and right ventricles. However, a subset of patients suffering from heart failure or other cardiovascular related diseases can have intact atrial-ventricular (AV) conduction to the right side of the heart, but can have a condition known as left bundle branch block (LBBB). LBBB is a cardiac condition where contraction of the left ventricle is delayed and/or non-existent, while contraction of the right ventricle is largely unaffected. LBBB can cause the left ventricle to contract later than the right ventricle or prevent the left ventricle from contracting. In certain cases, LBBB is currently treated with traditional pacemakers designed to pace the contraction of the heart.

A pacemaker is a battery-powered electronic device implanted under the skin and connected to the heart by an insulated metal lead wire with a tip electrode. Pacemakers were initially developed for and are most commonly used to treat bradycardia (slow heart rates), which can result from several conditions. More recently, advancements in pacemaker complexity, and associated sensing and pacing algorithms, have allowed progress in using pacemakers for the treatment of other conditions, notably heart failure (HF) and fast heart rhythms (tachyarrhythmia/tachycardia).

In a common application, pacemaker leads are placed through the skin into a subclavian vein or branch to access the venous side of the cardiovascular system. Such systems can be either single chamber with a lead placed in either the right atrium or right ventricle, or dual chamber systems with one lead placed in contact with the right atrial wall and a second lead placed in contact with the right ventricular wall. For the treatment of HF, through what is commonly known as cardiac resynchronization therapy, bi-ventricular pacing uses an additional (e.g., third) lead placed in contact with the left ventricle. To access the left ventricle, the third lead is typically advanced into the right atrium, through the orifice of the coronary sinus, and then maneuvered through the coronary sinus veins to a position on the epicardial aspect of the posterolateral or lateral wall of the left ventricle. In patients with LBBB, however, the leads can only be required to be placed in contact with the left ventricle.

Though now less common after several decades of improvement in designs and materials, failure of a pacemaker lead is still a significant risk to the patient—not only for the loss of pacing which can represent a life-threatening event, but also because extracting pacemaker leads after implantation involves significant risks. Additionally, the location of an existing non-functional lead, if not removable, can prevent implantation of a replacement lead. Pacemaker leads can fail due to several reasons including breakage of the insulator or conductor and loose or incompatible connectors.

DETAILED DESCRIPTION

The present technology is generally directed to wireless stimulation systems, devices, and methods that stimulate tissue by harvesting acoustic energy transmitted into the tissue and converting the acoustic energy into electrical energy which is then delivered to the tissue. More specifically, the present technology includes systems and methods for electrically stimulating the left side of the heart in a patient with intact right-side conduction (e.g., in a patient with Left Bundle Branch Block (LBBB)).

In some embodiments, a stimulation system includes a controller-transmitter configured to emit acoustic energy, and a receiver-stimulator configured to (i) receive the emitted acoustic energy, (ii) convert the acoustic energy to electrical energy, and (iii) deliver the electrical energy to adjacent tissue (e.g., to the left ventricle of a patient with LBBB). The controller-transmitter can include one or more sensors configured to detect real-time electrical activity of the heart. As the sensors detect certain aspects of the heart-beat, the controller-transmitter can emit acoustic energy that activates the receiver-stimulator, which then electrically stimulates the left side of the heart. If the electrical stimulation is applied to the left ventricle within a range of time immediately following the onset of right ventricular electrical conduction (e.g., QRS onset), the left ventricular pacing will synchronize with the right sided natural conduction to create a synchronized contraction of both ventricles.

In one aspect of the present technology, the stimulation system is configured to operate without wired leads and without a co-implanted conventional pacemaker system. In contrast, many conventional systems include a co-implanted device, such as a pacemaker device, that drives the pacing function. Accordingly, the present technology can include a stand-alone system that uses a controller-transmitter to drive the pacing in certain patients.

Figure 1A:
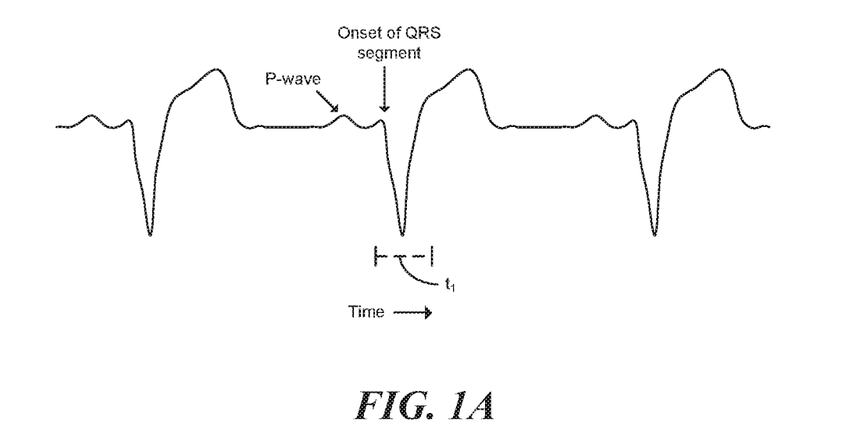
FIGS. 1A and 1B are schematic illustrations of electrocardiogram traces from a human suffering from Left Bundle Branch Block.

FIG. 1A is a schematic illustration of an electrocardiogram (ECG) trace of a patient having LBBB. As shown in FIG. 1A, a patient having LBBB will have a P-wave representing atrial depolarization that results in atrial contraction. Subsequently, the onset of the QRS segment is marked by a rapid deflection of the ECG trace and indicates the electrical signal for ventricular contraction. In the illustrated embodiment, the QRS segment has a duration $t_1$. Patients with LBBB will have a duration $t_1$ that is longer than the duration of the QRS segment in a healthy patient. For example, the duration $t_1$ for a patient with LBBB can be greater than about 120 milliseconds.

Figure 1B:
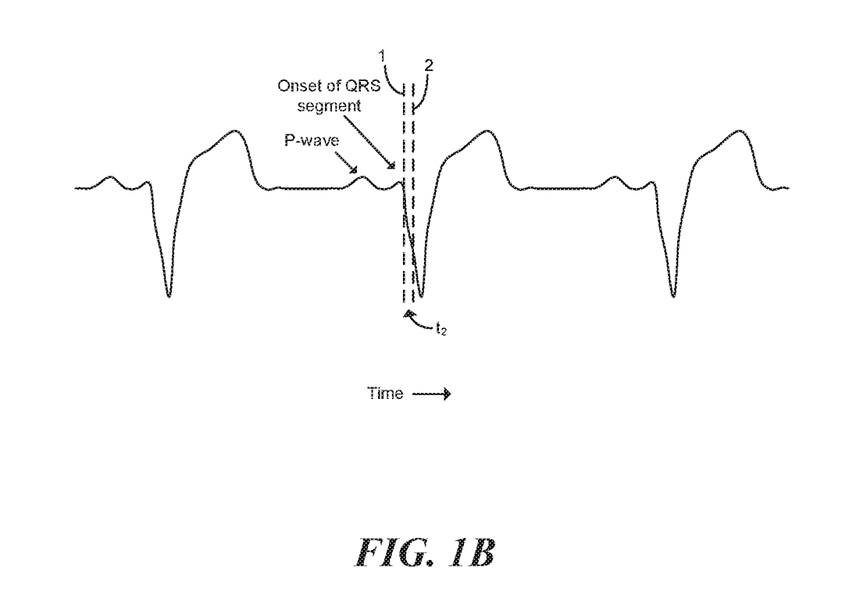

FIG. 1B is a schematic illustration of another ECG trace of a patient having LBBB. Dashed-line 1 in FIG. 1B illustrates the beginning of the QRS segment when the electrical signal initially depolarizes (e.g., to contract) the ventricles. However, the actual mechanical contraction of the ventricle happens sometime after the onset of the electrical signal to depolarize, as the electrical signal does not instantaneously cause the ventricles to contract. Thus, there is a range of time $t_2$ beginning at the onset of the QRS segment (e.g., at dashed-line 1) and terminating at dashed-line 2 in which electrical stimulation could be applied to the left ventricle to improve synchronization of the left ventricle and the right ventricle in patients with LBBB.

In some embodiments, the time $t_2$ can be between about 1 millisecond and 120 milliseconds. For example, the time $t_2$ can be about 1 millisecond, about 2 milliseconds, about 3 milliseconds, about 4 milliseconds, about 5 milliseconds, about 10 milliseconds, about 20 milliseconds, about 30 milliseconds, about 40 milliseconds, about 50 milliseconds, about 60 milliseconds, about 70 milliseconds, about 80 milliseconds, about 90 milliseconds, about 100 milliseconds, about 110 milliseconds, or about 120 milliseconds. If electrical stimulation is provided to the left ventricle within the time $t_2$, the left and right ventricles can have improved synchronization. In one aspect of the present technology, such stimulation of the left ventricle can shorten the overall duration of the QRS segment (indicated by $t_1$ in FIG. 1A) and/or improve the morphology of patients with LBBB.

Accordingly, the present technology includes systems and devices configured to stimulate the left ventricle within the duration $t_2$ to synchronize the contraction of the right and left ventricles. Furthermore, the systems and devices can be configured to detect the initiation of the QRS segment and, in response, determine when to initiate stimulation to ensure stimulation of the left ventricle within the duration $t_2$. For example, the system can initiate stimulation of the left ventricle immediately upon sensing initiation of the QRS segment. In other embodiments, the system can slightly delay initiating stimulation of the left ventricle after sensing initiation of the QRS segment. In other embodiments, the system can be configured to detect other cardiac conduction segments (e.g., the P-wave) and pace the stimulation of the left ventricle based off such segments. Because the systems and devices can both sense the electrical conduction of the heart and stimulate the heart in response to specific electrical signals (e.g., the initiation of the QRS segment), the present technology does not require a co-implanted pacemaker or external ECG leads to pace stimulation. Instead, the present technology provides systems and devices configured to effectively treat LBBB without co-implantation of another device.

Figure 2:
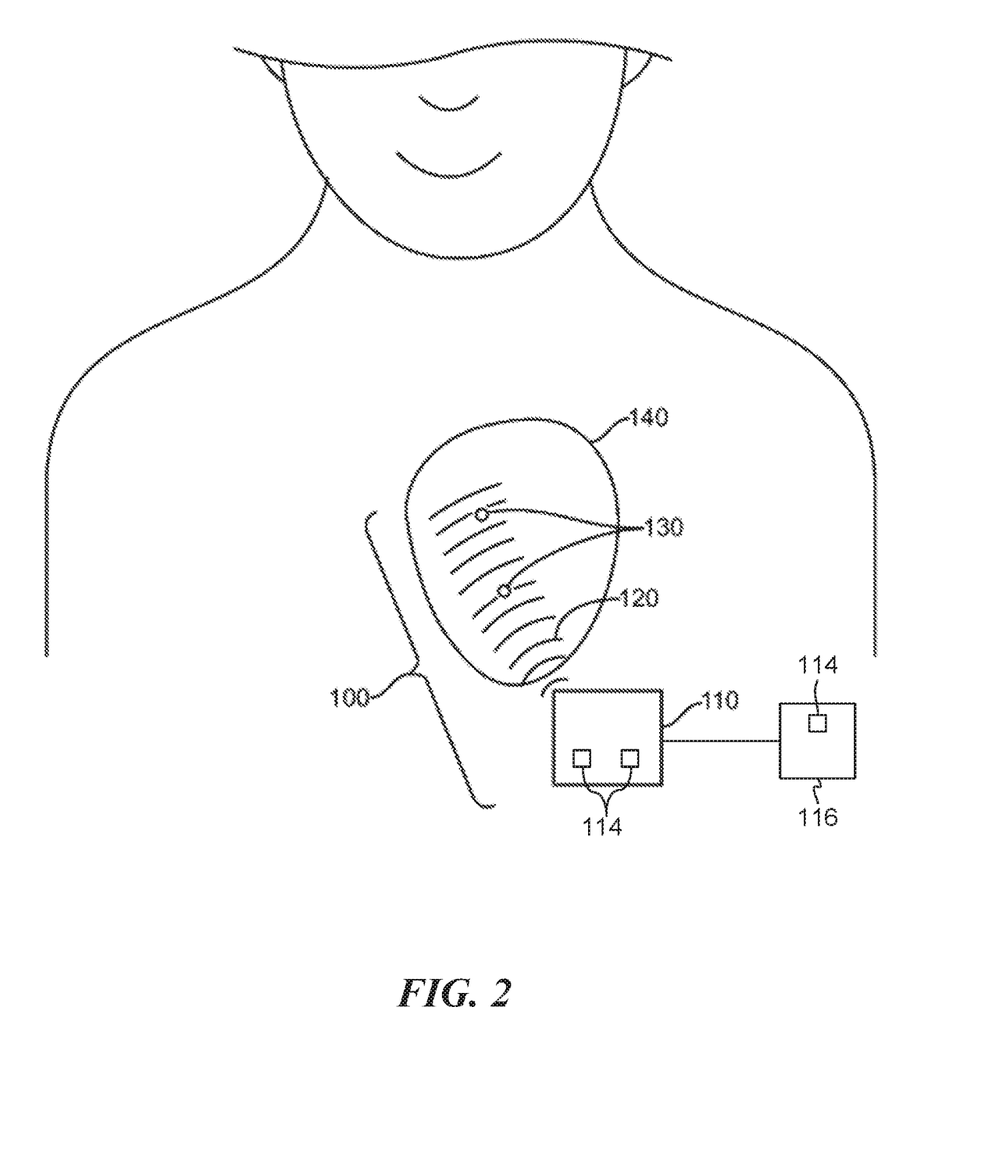
FIG. 2 is a partially-schematic view of a wireless tissue stimulation system configured to electrically stimulate a human heart in accordance with embodiments of the present technology.

FIG. 2 is a partially-schematic view of a wireless tissue stimulation system 100 configured to electrically stimulate a human heart 140 in accordance with embodiments of the present technology. In the illustrated embodiment, the wireless tissue stimulation system 100 includes an implantable or external controller-transmitter 110 and one or more receiver-stimulators 130 configured to be implanted in and/or positioned proximate to the heart 140. The controller-transmitter 110 generates acoustic energy 120 (e.g., an acoustic waveform, acoustic signal, etc.) of sufficient amplitude and frequency to allow the receiver-stimulators 130 to generate electrical energy for tissue stimulation. The receiver-stimulators 130 are configured to (i) harvest a portion of the acoustic energy 120, (ii) convert the harvested acoustic energy 120 into electrical energy, and (iii) deliver the electrical energy to electrically stimulate tissue of the heart 140. In some embodiments, the wireless tissue stimulation system 100 can include features similar or identical to those of the leadless tissue stimulation systems described in detail in, for example: (i) U.S. Patent Application Publication No. 2006/0136004, titled "LEADLESS TISSUE STIMULATION SYSTEMS AND METHODS," and filed Dec. 21, 2005; and (ii) U.S. Pat. No. 7,610,092, titled "LEADLESS TISSUE STIMULATION SYSTEMS AND METHODS," and filed Dec. 11, 2005; each of which is incorporated by reference herein in its entirety.

The acoustic signal 120 generated and emitted by the controller-transmitter 110 can be defined through several characteristics. For example, the acoustic signal 120 can operate at a frequency between about 20 kHz and 10 MHz, between about 100 kHz and 1 MHz, or between about 200 kHz and 500 kHz. The acoustic signal 120 generated by the controller-transmitter 110 can further comprise pulse width and pulse amplitude information that can be used by the receiver-stimulators 130 to construct a corresponding electrical output. In some embodiments, the acoustic energy 120 can be emitted as a single burst or as multiple bursts.

The acoustic energy 120 propagates via an acoustic field whose acoustic intensity is defined as the amount of acoustic power passing through a cross-sectional area and can be expressed as Watts per square meter. The effective cross-sectional area of the receiver-stimulators 130 is defined as the area available for harvesting acoustic energy. In some embodiments, the receiver-stimulators 130 include an acoustic transducer assembly for converting acoustic energy into electrical energy. In some embodiments, the effective cross-sectional area of each of the receiver-stimulators 130 can be generally equal to the cross-sectional area of the acoustic transducer assembly. In practice, the effective area can be less than that, due to inefficiencies in harvesting and energy conversion. In one embodiment, the receiver-stimulators 130 further include a tissue attachment mechanism and a catheter delivery interface. Due to the tissue attachment mechanism, catheter delivery interface, and other components of the receiver-stimulators 130, the effective area can be substantially less than the cross-sectional area of the receiver-stimulators 130. In some embodiments, the receiver-stimulators 130 can have a cross-sectional area of about 10 mm and an estimated effective area of 2 mm² = $2 \cdot 10^{-6}$ m². In some embodiments, to stimulate the heart 140, the effective area of the receiver-stimulators 130 can result in a minimum acoustic field intensity of around:

$$\frac{0.34 \text{ mW}}{2 \times 10^{-6} \text{ m}^2} = \frac{170 \text{ W}}{\text{m}^2}$$

For example, the electrical energy sufficient to stimulate the heart 140 can be about 0.17 μJ for a 0.5 millisecond electrical pulse. This means that about 0.34 mW of power is delivered to the tissue during the 0.5 millisecond pacing pulse for sufficient stimulation of the heart 140.

In some embodiments, a single receiver-stimulator 130 can be implanted for single site pacing. In other embodiments, multiple of the receiver-stimulators 130 can be implanted. The receiver-stimulators 130 can be configured to stimulate (i) simultaneously by receiving the same transmitted acoustic energy, (ii) sequentially through fixed or programmable delays after receiving the same transmitted acoustic energy, (iii) or independently by responding only to signal information of the transmitted acoustic energy of a specific character (e.g., of a certain frequency, amplitude, or by other modulation or encoding of the acoustic waveform 120) intended to energize only that specific device or spatial focusing of the ultrasound beam.

The wireless tissue stimulation system 100 can further include a power source 116. The power source 116 can comprise a battery (e.g., a rechargeable battery) and/or a transmit power supply (e.g., a DC-DC converter or AC-DC converter). In some embodiments, the power source 116 can be external to the controller-transmitter 110 while, in other embodiments, the power source 116 can be adjacent to or attached to the controller-transmitter 110. As can be appreciated by one of skill in the art, several different power sources could be utilized in the present technology and are included within the scope of the present technology.

The controller-transmitter 110 and/or the power source 116 can also include one or more sensors 114 (e.g., sensing electrodes). The sensors 114 are configured to detect electrical conduction of the heart 140 in at least substantially real-time (e.g., in real-time or with a delay of less than about 5 milliseconds, less than about 4 milliseconds, less than about 3 milliseconds, less than about 2 milliseconds, or less than about 1 millisecond). For example, the sensors 114 can be configured to detect the beginning of the period in which the controller-transmitter 110 needs to emit acoustic energy 120 to initiate electrical stimulation of the heart 140 by the receiver-stimulators 130 (e.g., the sensors 114 can be configured to detect the onset of the QRS segment). Thus, in some embodiments, the sensors 114 are capable of detecting when the acoustic energy 120 should be emitted to ensure electrical stimulation is provided that will facilitate improved synchronization of the left and right ventricles of the heart 140. In some embodiments, the controller-transmitter 110 can include one, two, three, four, five, six, or seven or more of the sensors 114.

Figure 3:
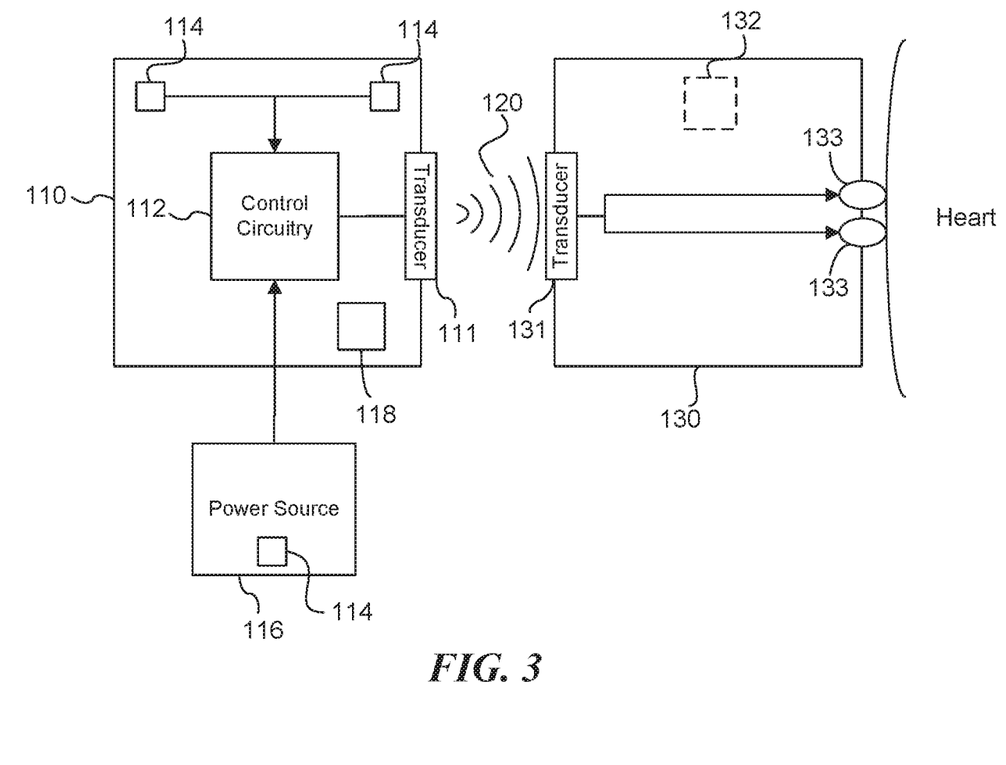
FIG. 3 is a block diagram of the stimulation system of FIG. 2 in accordance with embodiments of the present technology.

FIG. 3 is a block diagram of the wireless tissue stimulation system 100 of FIG. 2 illustrating further details of the wireless tissue stimulation system 100 in accordance with embodiments of the present technology. In the illustrated embodiment, the controller-transmitter 110 includes control circuitry 112 (e.g., a controller) and an output transducer assembly 111 for generating the acoustic energy 120 for transmission to the receiver-stimulators 130 (only a single one of the receiver-stimulators 130 is shown in FIG. 3 for the sake of clarity). The control circuitry 112 can include an amplifier configured to apply electrical energy to the transducer assembly 111, which in turn produces the acoustic energy 120 having selected characteristics/properties. The transducer assembly 111 can be a single transducer or can comprise multiple phased array transducers for steering and focusing the acoustic energy 120 on the receiver-stimulators 130. The control circuitry 112 can be connected to the sensors 114. As described above, the sensors 114 can be configured to detect electrical conduction of the heart and therefore drive the pacing of the controller-transmitter 110 and the receiver-stimulators 130.

The sensors 114 can be attached to or positioned within different aspects of the controller-transmitter 110 and/or the power source 116. For example, in some embodiments, the sensors 114 can be fully or partially disposed on an outer casing of the controller-transmitter 110. In some embodiments, the sensors 114 can be spaced apart from the controller-transmitter 110 and can be wirelessly connected to the controller-transmitter 110. In other embodiments, the sensors 114 can be connected to the controller-transmitter 110 via cables. In some embodiments, the sensors 114 can be disposed within a combination of the positions discussed herein. For example, when the wireless tissue stimulation system 100 includes two of the sensors 114, a first one of the sensors 114 can be attached to the power source 116 (e.g., to a battery) and a second one of the sensors 114 can be attached to the transducer assembly 111 of the controller-transmitter 110. When the wireless tissue stimulation system 100 includes four of the sensors 114, for example, three of the sensors 114 can be attached to the housing of the controller-transmitter 110 and the other one of the sensors 114 can be attached to the power source 116. As one skilled in the art will appreciate, a variety of sensor configurations based on the descriptions herein can be capable of sensing the electrical conduction of the heart in real-time and are within the scope of the present technology.

In some embodiments, the controller-transmitter 110 can further include a communication module 118. The communication module 118 can be configured to provide a data path (e.g., a radiofrequency (RF) communication path) to and/or from an external programmer unit to allow a physician to set device parameters and to acquire diagnostic information about the patient and/or the wireless tissue stimulation system 100.

The receiver-stimulators 130 can include a receiving transducer assembly 131 (e.g., a piezoelectric transducer assembly) configured to receive the acoustic energy 120 and convert the received acoustic energy into electrical energy. Optionally, the receiver-stimulators 130 can include a rectifier component (not shown). The optional rectifier component is used to convert the electrical energy to an electrical output which can be configured to effectively stimulate the tissue of the heart 140 (e.g., convert AC electrical energy into a DC output; but other output waveforms are also effective). In some embodiments, the electrical output of optional rectifier components is used to directly stimulate tissue. In an alternative embodiment, the receiver-stimulators 130 further include processing circuitry that manipulates the electrical output converted by the rectifiers to produce an electrical signal that stimulates tissue. The processing circuitry manipulates the electrical output such that it is suitable for the stimulation application, such as cardiac pacing. Such manipulation can involve summing or conditioning the electrical signals from the individual rectifiers to produce the biologically stimulating electrical output.

The receiver-stimulators 130 also include a tissue-contacting electrode assembly 133 configured to deliver an output voltage to stimulate the tissue. The electrode assembly 133 can include any number of stimulation electrodes (e.g., one, two, three, four, five, or more stimulation electrodes). In one embodiment, the electrode assembly 133 comprises at least two stimulation electrodes in electrical contact with the tissue. Either or both of the stimulation electrodes can be mounted directly on the receiver-stimulators 130 and form a portion of the receiver-stimulators 130 casing. In other embodiments, the stimulation electrodes can extend from the receiver-stimulators 130. In some embodiments, the electrode assembly 133 can include features generally similar or identical to those of the electrode assemblies described in U.S. Pat. No. 9,180,285, titled "IMPLANTABLE WIRELESS ACOUSTIC STIMULATORS WITH HIGH ENERGY CONVERSION EFFICIENCIES," and filed Oct. 21, 2013, which is incorporated herein by reference in its entirety.

The receiver-stimulators 130 can optionally include a voltage limiter 132 configured to limit the output voltage delivered to tissue by the electrode assembly 133. In one embodiment, the voltage limiter 132 is placed within the electrode assembly 133, such as between the stimulation electrodes. Alternatively, the voltage limiter 132 can be placed on the receiving transducer assembly 131, or anywhere between the receiving transducer assembly 131 and the electrode assembly 133, such that the voltage limiter 132 is able to limit the electrical voltage delivered to the tissue.

Referring to FIGS. 2 and 3 together, in one aspect of the present technology, in patients with right-side conduction intact, the wireless tissue stimulation system 100 can be utilized without a co-implant or leads because the sensors 114 are configured to detect the electrical conduction of the heart 140 in real-time. Accordingly, pacing of the controller-transmitter 110 and the receiver-stimulators 130 can be based off the electrical conduction of the heart 140 rather than signals received from a co-implant or from additional leads. This can be beneficial because, for example, it eliminates the need for implanting leads associated with traditional pacemaker systems.

Figure 4:
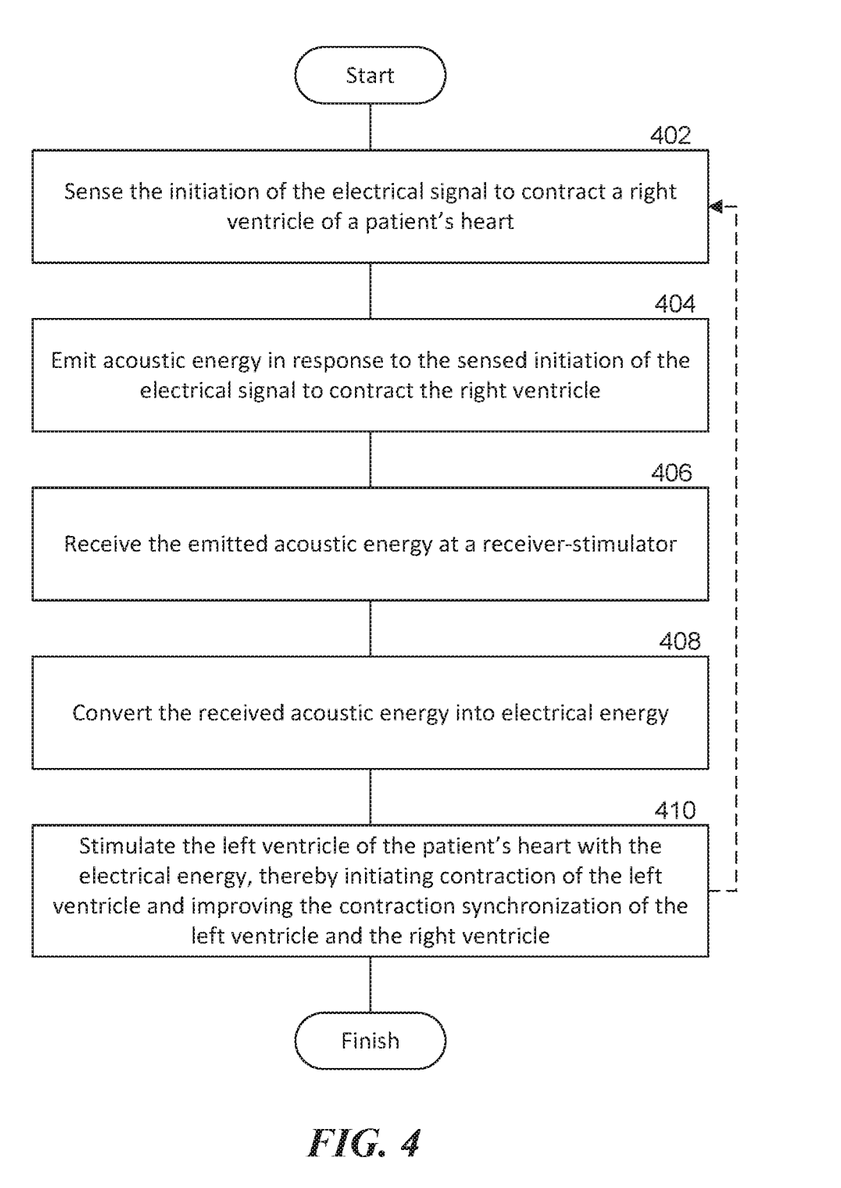
FIG. 4 is a flowchart of a process or method of stimulating a human heart in accordance with embodiments of the present technology.

The present technology also includes methods for synchronizing ventricular contraction in patients having LBBB. FIG. 4, for example, is a flowchart of a process or method 400 for stimulating the left ventricle of a heart of a patient having LBBB in accordance with embodiments of the present technology. Some aspects of the method 400 are described with reference to the wireless tissue stimulation system 100 of FIGS. 2 and 3, although other suitable systems can be used to carry out the method 400.

In the illustrated embodiment, the method 400 begins at block 402 by sensing the initiation of the electrical signal to contract the right ventricle of a patient's heart. The initiation of the electrical signal to contract the right ventricle corresponds with the onset of the QRS segment of the ECG reading. For example, the controller-transmitter 110 can detect the electrical conduction of the heart 140 in real-time using one or more of the sensors 114.

The method 400 continues at block 404 by emitting acoustic energy in response to the sensed initiation of the electrical signal to contract the right ventricle. The acoustic energy can be emitted, for example, by the transducer assembly 111 of the controller-transmitter 110. The controller-transmitter 110 can determine when to emit the acoustic energy in response to the sensed initiation of the electrical signal (e.g., immediately or with a slight delay) to facilitate synchronization.

Next, the method 400 includes (i) receiving the emitted acoustic energy at a receiver-stimulator (block 406) and (ii) converting the received acoustic energy into electrical energy (block 408). For example, the one or more of the receiver-stimulators 130 can receive the acoustic energy 120 and convert the acoustic energy to electrical energy via the receiving transducer assemblies 131.

At block 410, the method 400 continues by stimulating the left ventricle of the patient's heart with the electrical energy. The stimulation can initiate contraction of the left ventricle and improve the contraction synchronization of the left ventricle and the right ventricle. Accordingly, the stimulation can be provided within a specified duration wherein stimulation of the left ventricle will synchronize the contraction of the left and right ventricles. As described in detail above with reference to FIGS. 1A and 1B, the duration can be between about 1 millisecond to 120 milliseconds after the initiation of the QRS complex.

The method 400 can return to block 402 and be repeated any number of times to provide continuous stimulation and synchronization of the heart.

The following examples are illustrative of several embodiments of the present technology:

1. A wireless system for stimulating the left ventricle of a heart of a human subject having LBBB, the system comprising:
   a controller-transmitter configured to be implanted in the human subject, the controller-transmitter including—
      one or more sensors configured to receive an indication of electrical conduction of the heart,
      a controller operably coupled to the one or more sensors and configured to determine, in substantially real-time, an occurrence of the electrical conduction of the heart, and
      a first transducer operably coupled to the controller and configured to emit an acoustic signal in response to the controller determining the occurrence of the electrical conduction of the heart; and
   a receiver-stimulator configured to be implanted adjacent to the left ventricle of the human subject, the receiver-stimulator including—
      a second transducer configured to (a) receive the acoustic signal emitted from the first transducer and (b) convert the received acoustic signal into electrical energy, and
      one or more stimulation electrodes coupled to the second transducer and configured to deliver the electrical energy to the left ventricle of the heart as electrical stimulation;
   wherein the system is configured to synchronize contraction of the left ventricle and a right ventricle of the heart by delivering the electrical stimulation to the left ventricle within a predefined duration beginning at an onset of the electrical conduction of the heart.

2. The wireless system of example 1 wherein the one or more sensors are configured to detect the electrical conduction of the heart with a delay of less than about 5 milliseconds, less than about 4 milliseconds, less than about 3 milliseconds, less than about 2 milliseconds, or less than about 1 millisecond.

3. The wireless system of example 1 or example 2 wherein the first transducer is configured to emit the acoustic signal in response to the one or more sensors sensing the initiation of a QRS segment.

4. The wireless system of any one of examples 1-3 wherein the predefined duration is less than about 10 milliseconds.

5. The wireless system of any one of examples 1-3 wherein the predefined duration is about 1 millisecond, about 2 milliseconds, about 3 milliseconds, about 4 milliseconds, about 5 milliseconds, about 10 milliseconds, about 20 milliseconds, about 30 milliseconds, about 40 milliseconds, about 50 milliseconds, about 60 milliseconds, about 70 milliseconds, about 80 milliseconds, about 90 milliseconds, about 100 milliseconds, about 110 milliseconds, or about 120 milliseconds.

6. The wireless system of any one of examples 1-5 wherein the controller-transmitter further comprises a battery and a battery housing, and wherein at least one of the one or more sensors is attached to the battery housing.

7. The wireless system of any one of examples 1-6 wherein the controller-transmitter further comprises a housing, and wherein at least one of the one or more sensors is attached to the housing.

8. The wireless system of any one of examples 1-7 wherein the controller-transmitter further comprises a housing, a battery, and a battery housing, and wherein the one or more sensors include a first sensor and a second sensor, wherein the first sensor is attached to the controller-transmitter housing, and wherein the second sensor is attached to the battery housing.

9. The wireless system of any one of examples 1-8 wherein the electrical conduction of the heart is at the onset of a QRS segment.

10. The wireless system of any one of examples 1-9 wherein the receiver-stimulator further includes a rectifier component configured to convert the electrical energy into an electrical output configured to stimulate the left ventricle.

11. The wireless system of example 10 wherein the rectifier component is configured to convert AC electrical energy into DC electrical output.

12. The wireless system of any one of examples 1-11, further comprising a second receiver-stimulator configured to be implanted adjacent to the left ventricle of the human subject.

13. The wireless system of any one of examples 1-12, wherein the controller-transmitter further comprises a communication module configured to provide a data path to an external programmer unit.

14. A method for stimulating the left ventricle of a heart of a human subject having LBBB, the method including:
sensing the initiation of an electrical signal to contract a right ventricle of the heart by detecting the onset of a QRS segment;
emitting acoustic energy in response to the sensed initiation of the electrical signal to contract the right ventricle, wherein the acoustic energy is emitted by a controller-transmitter;
receiving the emitted acoustic energy at a receiver-stimulator implanted within or adjacent to the left ventricle;
converting the received acoustic energy into electrical energy; and
stimulating the left ventricle with the electrical energy, wherein the electrical energy is sufficient to initiate contraction of the left ventricle, and wherein the stimulation of the left ventricle improves the contraction synchronization of the left ventricle and the right ventricle.

15. The method of example 14 wherein stimulating the left ventricle occurs within about 1 millisecond, about 2 milliseconds, about 3 milliseconds, about 4 milliseconds, about 5 milliseconds, about 10 milliseconds, about 20 milliseconds, about 30 milliseconds, about 40 milliseconds, about 50 milliseconds, about 60 milliseconds, about 70 milliseconds, about 80 milliseconds, about 90 milliseconds, about 100 milliseconds, about 110 milliseconds, or about 120 milliseconds of sensing the initiation of the QRS segment.

16. The method of example 14 or example 15 wherein stimulating the left ventricle reduces the duration of the QRS segment.

17. The method of any one of examples 14-16 wherein sensing the initiation of the electrical signal and emitting the acoustic energy includes providing a controller-transmitter implanted inside the human subject.

18. The method of any one of examples 14-17 wherein sensing the initiation of the electrical signal includes providing one or more sensors configured to detect an electrical conduction of a heart in real-time or with a delay of less than about 5 milliseconds, less than about 4 milliseconds, less than about 3 milliseconds, less than about 2 milliseconds, or less than about 1 millisecond.

19. The method of any one of examples 14-18 wherein the receiver-stimulator is one of a plurality of receiver-stimulators, and wherein stimulating the left ventricle includes stimulating the left ventricle with the plurality of receiver-stimulators.

20. The method of any one of examples 14-19 wherein sensing the initiation of the electrical signal includes sensing consecutive electrical signals corresponding to consecutive QRS segments, and wherein stimulating the left ventricle includes stimulating the left ventricle in consecutive cycles to mimic a heartbeat.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the art will recognize. In some cases, well-known structures and functions have not been shown or described in detail to avoid unnecessarily obscuring the description of the embodiments of the present technology. Although steps of methods can be presented herein in a particular order, alternative embodiments can perform the steps in a different order. Similarly, certain aspects of the present technology disclosed in the context of particular embodiments can be combined or eliminated in other embodiments. Furthermore, while advantages associated with certain embodiments of the present technology can have been disclosed in the context of those embodiments, other embodiments of the present technology can have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of items in the list. Use of the term "about" refers to the stated value plus or minus 10%. Additionally, the term "comprising" is used throughout to mean including at least the recited feature(s) such that any greater number of the same feature and/or additional types of other features are not precluded. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics can be combined in any suitable manner in one or more embodiments.

We claim:

1. A wireless system for stimulating the left ventricle of a heart of a human subject having left bundle branch block (LBBB), the system comprising:
a controller-transmitter configured to be implanted in the human subject, the controller-transmitter including—
one or more sensors configured to receive an indication of electrical conduction of the heart,
a controller operably coupled to the one or more sensors and configured to determine, in substantially real-time, an occurrence of an onset of a QRS segment in the electrical conduction of the heart, and
a first transducer operably coupled to the controller and configured to emit an acoustic signal in response to the controller determining the occurrence of the onset of the QRS segment in the electrical conduction of the heart; and
a receiver-stimulator configured to be implanted adjacent to the left ventricle of the human subject, the receiver-stimulator including—
a second transducer configured to (a) receive the acoustic signal emitted from the first transducer and (b) convert the received acoustic signal into electrical energy, and
one or more stimulation electrodes coupled to the second transducer and configured to deliver the electrical energy to the left ventricle of the heart as electrical stimulation;
wherein the system is configured to synchronize contraction of the left ventricle and a right ventricle of the heart by delivering the electrical stimulation to the left ventricle within a predefined duration beginning at the onset of the QRS segment in the electrical conduction of the heart.

2. The wireless system of claim 1 wherein the one or more sensors are configured to detect the electrical conduction of the heart with a delay of less than about 5 milliseconds, less than about 4 milliseconds, less than about 3 milliseconds, less than about 2 milliseconds, or less than about 1 millisecond.

3. The wireless system of claim 1 wherein the predefined duration is less than about 10 milliseconds.

4. The wireless system of claim 1 wherein the predefined duration is about 1 millisecond, about 2 milliseconds, about 3 milliseconds, about 4 milliseconds, about 5 milliseconds, about 10 milliseconds, about 20 milliseconds, about 30 milliseconds, about 40 milliseconds, about 50 milliseconds, about 60 milliseconds, about 70 milliseconds, about 80 milliseconds, about 90 milliseconds, about 100 milliseconds, about 110 milliseconds, or about 120 milliseconds.

5. The wireless system of claim 1 wherein the controller-transmitter further comprises a battery and a battery housing, and wherein at least one of the one or more sensors is attached to the battery housing.

6. The wireless system of claim 1 wherein the controller-transmitter further comprises a housing, and wherein at least one of the one or more sensors is attached to the housing.

7. The wireless system of claim 1 wherein the controller-transmitter further comprises a housing, a battery, and a battery housing, and wherein the one or more sensors include a first sensor and a second sensor, wherein the first sensor is attached to the controller-transmitter housing, and wherein the second sensor is attached to the battery housing.

8. The wireless system of claim 1 wherein the receiver-stimulator further includes a rectifier component configured to convert the electrical energy into an electrical output configured to stimulate the left ventricle.

9. The wireless system of claim 8 wherein the rectifier component is configured to convert AC electrical energy into DC electrical output.

10. The wireless system of claim 1, further comprising a second receiver-stimulator configured to be implanted adjacent to the left ventricle of the human subject.

11. The wireless system of claim 1, wherein the controller-transmitter further comprises a communication module configured to provide a data path to an external programmer unit.

* * * * *